United States Patent
Puchnin et al.

(10) Patent No.: US 10,139,327 B2
(45) Date of Patent: Nov. 27, 2018

(54) INDENTATION DEVICE, INSTRUMENTED MEASUREMENT SYSTEM, AND A METHOD FOR DETERMINING THE MECHANICAL PROPERTIES OF MATERIALS BY THE INDENTATION METHOD

(71) Applicant: Ceske Vysoke Uceni Technicke v Praze, Fakulta Strojni, Prague (CZ)

(72) Inventors: Maxim Puchnin, Praha (CZ); Evgeniy Anisimov, Praha (CZ); Frantiska Peslova, Ceska Trebova (CZ)

(73) Assignee: CESKE VYSOKE UCENI TECHNICKE V PRAZE, FAKULTA STROJNI, Prague (CZ)

( * ) Notice: Subject to any disclaimer, the term of this patent is extended or adjusted under 35 U.S.C. 154(b) by 108 days.

(21) Appl. No.: 14/787,592

(22) PCT Filed: Oct. 13, 2015

(86) PCT No.: PCT/CZ2015/001119
§ 371 (c)(1),
(2) Date: Oct. 28, 2015

(65) Prior Publication Data
US 2016/0377518 A1    Dec. 29, 2016

(30) Foreign Application Priority Data
Jun. 23, 2015    (CZ) .............................. PV 2015-420

(51) Int. Cl.
*G01N 3/00*    (2006.01)
*G01N 3/42*    (2006.01)
(Continued)

(52) U.S. Cl.
CPC ............... *G01N 3/42* (2013.01); *G01B 7/003* (2013.01); *G01B 7/26* (2013.01); *G01N 19/04* (2013.01)

(58) Field of Classification Search
CPC .................................. G01N 3/42; G01N 19/04
(Continued)

(56) References Cited

U.S. PATENT DOCUMENTS 4,435,976 A * 3/1984 Edward, Jr. ............... G01N 3/44
                                                           73/83
4,567,774 A * 2/1986 Manahan ................. G01N 3/00
                                                          374/49
(Continued)

FOREIGN PATENT DOCUMENTS

| CZ | 304 637 | 8/2014 |
| GB | 2 161 279 | 1/1986 |
| WO | 2013/135026 | 9/2013 |

*Primary Examiner* — John Fitzgerald
*Assistant Examiner* — Rodney T Frank
(74) *Attorney, Agent, or Firm* — Jacobson Holman, PLLC.

(57) ABSTRACT

The instrumented indentation measurement system includes an indentation device, a loading mechanism, a table for the sample, an analog-digital converter and a computer. Inside a housing of the device there is arranged a holder for a displacement sensor, rigidly connected to the housing. Slidably positioned rod passing to the displacement sensor is arranged in the holder in the axis of the indenter. A pushing segment is equipped with supports engaging with a central pressure plate arranged slidably in the housing a lower pressure plate is arranged slidably in the housing and connected with the holder of the indenter. A first resilient member, a central pressure plate and the lower pressure plate are provided with holes for passage of the rod to the holder.

14 Claims, 11 Drawing Sheets

(51) Int. Cl.
  *G01B 7/26*    (2006.01)
  *G01B 7/00*    (2006.01)
  *G01N 19/04*   (2006.01)

(58) Field of Classification Search
  USPC ........................................................ 73/12.09
  See application file for complete search history.

(56) References Cited

U.S. PATENT DOCUMENTS

| | | | |
|---|---|---|---|
| 4,852,397 A | 8/1989 | Haggag | |
| 5,357,786 A * | 10/1994 | Lung | G01N 3/42 73/81 |
| 5,916,009 A * | 6/1999 | Izumi | B24B 37/04 257/E21.237 |
| 6,112,589 A * | 9/2000 | Tressler | G01M 11/088 73/159 |
| 6,134,954 A * | 10/2000 | Suresh | G01N 3/42 702/156 |
| 6,247,356 B1 * | 6/2001 | Merck, Jr. | G01N 3/42 73/82 |
| 6,679,124 B2 * | 1/2004 | Oliver | G01N 3/08 73/796 |
| 6,718,820 B2 * | 4/2004 | Kwon | G01N 3/48 73/81 |
| 7,681,459 B1 * | 3/2010 | Yang | G01N 3/08 73/760 |
| 7,966,866 B2 * | 6/2011 | Hansma | A61B 5/0053 73/81 |
| 2002/0106625 A1 * | 8/2002 | Hung | C12M 21/08 435/1.1 |
| 2003/0054740 A1 * | 3/2003 | Mansky | G01N 3/02 451/57 |
| 2003/0226404 A1 * | 12/2003 | Ouellet | G01N 3/20 73/849 |
| 2007/0276292 A1 * | 11/2007 | Hansma | A61B 5/4504 600/587 |
| 2009/0056427 A1 * | 3/2009 | Hansma | A61B 5/0053 73/82 |
| 2009/0093692 A1 * | 4/2009 | Hansma | A61B 5/103 600/306 |
| 2009/0107296 A1 * | 4/2009 | Tachino | F01L 1/20 81/9.24 |
| 2009/0165538 A1 * | 7/2009 | Sawa | G01N 3/42 73/81 |
| 2010/0135860 A1 * | 6/2010 | Halamis | B01L 3/5025 422/400 |
| 2010/0294147 A1 * | 11/2010 | Loiret-Bernal | B41F 19/068 101/41 |
| 2011/0132078 A1 * | 6/2011 | Wu | G01N 3/08 73/81 |
| 2011/0162430 A1 * | 7/2011 | Nishimura | B23P 9/025 72/334 |
| 2011/0174036 A1 | 7/2011 | Mauvoisin | |
| 2011/0234057 A1 * | 9/2011 | Piaton | H02K 29/08 310/68 B |
| 2011/0304750 A1 | 12/2011 | Lee et al. | |
| 2012/0049412 A1 * | 3/2012 | Middlebeek | A61J 3/10 264/299 |
| 2012/0304750 A1 | 12/2012 | Mauvoisin | |
| 2014/0047885 A1 * | 2/2014 | Battenfeld | H01R 43/0486 72/21.4 |
| 2016/0126213 A1 * | 5/2016 | Celia, Jr. | B23K 37/0408 228/101 |

\* cited by examiner

INDENTATION DEVICE, INSTRUMENTED MEASUREMENT SYSTEM, AND A METHOD FOR DETERMINING THE MECHANICAL PROPERTIES OF MATERIALS BY THE INDENTATION METHOD

FIELD OF THE INVENTION

The invention relates to the field of testing and measuring the mechanical properties of materials using a nondestructive method, specifically an indentation device using an instrumented measurement system.

BACKGROUND OF THE INVENTION

The mechanical properties of materials can be examined by means of several principally different methods that are used in engineering design as well as quality control and life estimation of machine parts and structures. The methodological approaches can be divided into destructive and nondestructive methods, where the latter is an alternative method since it allows for the execution of tests directly on a structural component and/or even during operation without the need of manufacturing the special standardized samples. Nondestructive methods are usually less time-consuming, less labor-intensive, and they are energy-efficient. This is possible due to high sensitivity, resolution, and stability of the sensing elements of the testing device, coupled with its compact design and advanced automation on the hardware and software levels. A relatively simple non-destructive test based on the instrumented indentation method provides the user with a wide range of material properties such as hardness, modulus of elasticity, yield strength, tensile strength, and fracture strength, energies of elastic and plastic deformations, strain hardening exponent, etc.

The hardness measurement is normally carried out by the indentation method, in which an indenter with defined geometric parameters penetrates into the surface of the test sample. The hardness number is determined by measuring the geometrical parameters of the indentation made by the indenter. For example, indentation diameter, indentation depth or displacement of the indenter at the given load, are among the measured values. Other mechanical properties of the material can be subsequently obtained from the measured numerical values of hardness using known and standardized relationships.

In the instrumented measuring systems based on the indentation method, the accuracy of measured penetration depth (linear displacement) of the indenter is important. This accuracy depends on the sensitivity of the device, location of the displacement sensor and its resolution. Relatively small displacements are usually measured by the use of lasers, strain gauges, electromagnetic sensors etc. The measurement accuracy and reproducibility of the results can be influenced by a number of factors, including the location of the displacement sensor as well as the distance and the number of other elements embedded between the sensor and the indenter, which stress-strain states may depend on the loading conditions and the number of cycles, etc. The loading conditions during the test should not affect the functioning of the sensors and indentation device; therefore, a proper design of the indentation device is needed to eliminate the excessive loads of its parts.

Among the disadvantages of known instrumented indentation devices are their use in the limited loading ranges, and/or the types of available indenters are also limited.

Patent CZ 304637 describes an indentation device that comprises a housing in which there is an adapter with a spring, a displacement sensor, and a load cell. The displacement sensor is equipped with a deformable strip and a strain gauge, cylinder, and a rod extending from the indenter to the displacement sensor. The load cell is equipped with multiple deformable strips and the strain gauges. The advantage of the displacement sensor is in its shape, which is formed as an exchangeable capsule that has several possible designs, including a lever multiplier, a deformation bridge or deformation strip, all provided with the strain gauges and an attachment place for the rod. The load cell is also exchangeable and has deformable strips with the strain gauges designed to measure the low loads, and a cylinder with the strain gauges designed to measure the high loads, all connected to an analog signal amplifier and a computer. The adapter can be used to connect the measuring head to various loading mechanisms such as a hardness tester, tensile machine, lever mechanism, etc. The measurement system is also equipped with an analog-digital converter and a computer with a software module, which is used to record the measured parameters of the indentation and for calculation of mechanical and physical properties. The disadvantages of this indentation device is in its large dimensions, it requires the use of mechanical loading devices, which implies that its manual application during measuring is not possible, and that the accuracy and reproducibility of the measurement is not within a sufficiently wide measuring range.

The possibility of counting the mechanical properties such as modulus of elasticity, yield strength, etc. is mentioned only generally, with the measured data of indenter penetration depth and applied force, without the description of a specific method.

Document U.S. Pat. No. 6,718,820 describes several measurement systems, including portable systems that can be attached to the tested body, or to a system with a movable table, or to an assembly with its own loading mechanism, in which the indenter displacement sensor is located next to the indenter and their geometric axes which are parallel to each other. This design may generate an error during the measurement of the indentation depth, especially at the loads as high as 3000 kgf, due to deformation of the components adjacent to the indentation device. This may be the indenter, the indenter holder, etc., thereby reducing the accuracy of the measurement. The maximum load of the load cell is 300 kgf with the deviation of 2.5 to 5.6 g. Such a low load forces limit the use of larger indenters, e.g. with a diameter of 10 mm and larger.

Patent application US 2011/0174036 describes a measuring device for curved samples, where between the table and the sample there is inserted a sphere with the appropriate diameter so that during the indentation the sample positioned correctly and the correct values are measured. There are three displacement sensors placed around the indenter at the angle of 120° to increase the accuracy of measurement of the displacement, where the final signal is averaged. This design does not address the issue of the deformation of the components surrounding the indenter. The use of three sensors significantly increases the cost, complicates the design, and increases demands on handling.

Patent application US 2012/0304750 describes a portable measuring system that fits in the palm and the load can be induced by the hand, or robot, or by a manipulator. The displacement sensors are located in the same manner as in US 2011/0174036.

The device according to U.S. Pat. No. 4,852,397, among similar features of the other designs, also has an ultrasonic sensor for measuring the size of the cracks in the vicinity of the indentation and also describes its own methodology for calculating the residual stresses. The displacement sensor is similar to those used in other systems, and is located next to the indenter, wherein the ultrasonic sensor, indenter, and displacement sensor are in one line. This greatly increases the minimum size of the measurable sample, since these elements must touch the sample surface. Another disadvantage is that the sensor may be damaged by improper handling of the sample. The patent gives its own methodology for calculating the mechanical properties of materials and plot of the stress-strain diagram.

U.S. Pat. No. 6,134,954 describes an indentation device which consists of two parts. In the top part there is a load cell, an indenter, and a displacement sensor. In the bottom part there is a sample holder and a mirror for the displacement sensor. The bottom part is placed on a movable table to move the indenter to the specimen. Parts of the indentation device can be bolted to the loading mechanism. The displacement sensor is located out of the load axis and its distance to the indenter is large, this design is also limited to the loading range of up to 500N with an accuracy of 0.02 to 0.1 N, and the accuracy of the depth measurement is in the range of 0.1-0.5 microns. The patent describes its own methodology for calculating the mechanical properties of the material and the plot of the stress-strain diagram.

The indentation device ZWICK (available from www.zwick.cz/cs/media.html), based on patent GB 2161279 A and other patent documents, has an indentation device with integrated loading mechanism, housing that comprises a displacement sensor with a resolution of 0.02 microns. The displacement of the indenter is measured with respect to the housing using a scale located on the indentation surface. Measurement of the indentation geometry is provided by an optical system in combination with a manual or motorized table. The elastic deformations during the test may negatively influence the accuracy of measurement. The accuracy of the load cell is 1% with two measuring ranges, 2 to 200N and 5 to 2500N. The device enables the use of different indenters and is fully automated, but besides the hardness and plot of indentation curve, there are no other mechanical parameters calculated. The device is large, with a height of about 1 m and weighing about 100 kg.

Document U.S. Pat. No. 4,435,976 describes a device for measuring the hardness of a material with an indentation device which is connected to the operating member for the application of the first preset lower load force followed by the subsequent application of a second preset greater load force. The central rod of the indenter displacement sensor is divided and the strain gauges are placed in the axis of the rod. The rod is mounted in bearings permitting its movement in an axial direction while from the top, hydraulic pistons push on it with different preset load forces. The disadvantage of this design consists in the necessity of using a special hydraulic circuit for applying the load force and in that the rod of the displacement sensor is affected by the load force.

Document WO2013135026A1 describes a portable digital device for measuring the hardness of a material and also has a support saddle, a compression head, an electronic circuit, a digital display, and a device for measuring pressure and the depth of indentation. This device consists of a rotary hand wheel, rotary encoder, sleeves, and a micrometer composed of a nut and bolt. The rotary encoder is mounted on the support saddle. The rotating shaft of the rotary encoder is coupled to the micrometer bolt and rotates with it. The upper end of the micrometer bolt is connected to a rotating wheel, the bottom end is connected to a pressure gauge, and the lower part of the pressure gauge is connected to the pressure head. The rotary wheel, micrometer bolt, device for measuring pressure, and the pressure head are all interconnected and have a common longitudinal axis, and the movement is provided by the rotation of the rotary hand wheel in the axial direction. The advantage of this device is in its simple design and manipulation. The device allows for the measurement of only hardness values, and with low accuracy.

The disadvantages of known indentation devices and instrumented measuring systems used for measuring mechanical properties of materials by the indentation method consist mainly in the fact that there is no device available that would completely eliminate the influence of deformation on the measurement of displacement caused by the action of the load force, which would also permit the testing of product materials using a nondestructive method in a wide range of load forces, e.g. from 1N to 35 kN with adequate accuracy and reproducibility of results, which would be small in size and low-weight while allowing connection to the various loading mechanisms including manual application, and which would be compact with an effective protection of all sensors so that the device would be usable even in aggressive environments and would withstand rough handling.

SUMMARY OF THE INVENTION

The above-mentioned disadvantages of the known designs are eliminated by an indentation device with an instrumented measuring mechanism and the possibility of using various methods for measuring the mechanical properties of materials by the indentation method according to the present invention.

The present invention is a measuring device for measuring the mechanical properties of materials, consisting of a housing provided with a facing with a hole, and a holder for the indenter placed in the hole of the facing with the sliding rod resting on the indenter. The device is further equipped with a displacement sensor, load cell, and a pushing segment for loading the indenter holder. The essential principle of the invention consists in the fact that inside the housing there is arranged holder for the displacement sensor which is rigidly connected to the housing, in which there is slidably positioned a rod passing to the displacement sensor anchored by the holder in the axis of the indenter. The movable pushing segment in the upper part of the housing is provided with at least one support passing within the vicinity of the holder and which is engaged with the central pressure plate, precisely and slidably positioned in the housing. The central pressure plate carries at least one load cell with deformable protrusions. The deformable protrusions abut across the gap to a lower pressure plate and movably mounted in the housing and connected to the indenter holder, wherein between the lower pressure plate and the facing there is located the first resilient member. The central pressure plate and the lower pressure plate are provided with holes for passage of the rod sliding into the holder.

Another preferred embodiment of the invention consists in the fact that the housing of a cylindrical shape has an internal mount created above, in which the holder is fixed by means of bolts; in the middle of the holder there is a hole for the rod with precisely placed displacement sensor, whereby the hole is covered on the upper side of the holder by a cap fastened with bolts to the holder.

In another preferred embodiment of the invention, the movable pushing segment with two supports that rest on the central pressure plate has, in order, a second load cell centered on the central pressure plate, wherein the accuracy of the second load cell is at least 10 times lower than the maximum load force of the first load cell. The value of maximum deformation of the deformable protrusions of the first load cell at maximum load corresponds to the width of the gap. Advantageously, it is possible to utilize the measurement range of the first load cell to 150 N and the measuring range of the second load cell to 35 kN.

In another preferred embodiment of the invention, the sensor holder has, on its lower part, a centering guide tube positioned in the middle of the hole of the second load cell, wherein the central pressure plate is provided with an axial recess in which there are mounted the first two load cells on the rod which passes through this recess and is slidably positioned in the guide tube.

In another preferred embodiment of the invention, the facing has a peripheral flange in which there is set a housing and central supporting segment having a hole in which there is slidably placed a guide collar of the lower pressure plate, in which there is fastened the indenter holder, and the first resilient member comprises a compression spring placed between the bottom pressure plate and the facing.

Preferably, the rod passes through the central hole of the displacement sensor which is touch sensitive or magnetic.

In another preferred embodiment of the invention, the pushing segment is provided with a threaded hole for connection to the loading mechanism.

Another preferred embodiment of the invention is designed for measuring in special environments where the length of the supporting segment is greater than the length of the indenter holder.

In another preferred embodiment, the indentation device includes an external chamber for testing samples of the material in a simulated environment, the chamber is closed by a removable cover with a hole for the indenter, inside the chamber there are slidable jaws for clamping the sample which are connected to micrometric bolts protruding from the housing chamber, and the chamber is further provided with a small window made of transparent material for observation of the sample.

In another preferred embodiment, the pushing segment is adapted for handling without the loading mechanism, the first resilient member comprises a rubber pad, and between the pushing segment and the housing there is arranged a second resilient member also comprising a rubber pad and a return spring.

In a preferred embodiment of the displacement sensor, the rod in the upper part is quadrangular and provided with a magnetic tape, and slidably positioned in a quadrangular hole in the holder of a displacement sensor, which comprises the magnetic sensor positioned against the magnetic tape.

In another preferred embodiment of the invention intended for manual measuring, the housing with facing form an integrated unit, the lower base of the facing is flat, the upper surface of the pushing segment is convex, and the lower pressure plate has a guide collar in which there is mounted the indenter holder which is slidably positioned in the hole of the facing. The manual indentation device may have an integrated display for displaying during the course of the measurement.

The main advantage of the indentation device and instrumented measuring system according to the invention lies in the fact that the construction allows for accurate measurement of the displacement of the indenter without a deformation effect to the relevant parts, within a wide range of loads, with excellent or adequate accuracy in an entire range of load forces through the elimination of all distortion of the components connected with the measurement of movement. In the embodiment with a combination of two load cells, forces can be measured in a range from 0.01 N to 35 N. Measurement of the movement takes place in the axis of loading, directly from the indenter to eliminate the deformation of the indenter holder and other nearby components, while eliminating the occurrence of signal variations or "creeping". The device enables the evaluation of the mechanical properties of engineering and construction materials, metals, ceramics, plastics, composites, concrete, etc. The simple principle of the device and its resistance allow for its outdoor use, e.g. for the reliable, accurate, and repeatable inspection of the material of construction and power equipment, welded joints etc., as well as for use in aggressive environments.

The construction is designed so that all the sensors are located inside the indentation device so as to be protected from damage while handling the sample or the environment. The device can also be operated by trained personnel. This device can be, without problem, bolted to another loading mechanism, equipped with its own loading mechanism, or used as an option for manual measurements.

Based on the methodology of the invention, the following can be determined from the measurements by calculation: Brinell hardness HB; Martens hardness HM; Vickers hardness HV; HRC, HRA, and HK hardness, contact radius of indentation a, material hardening coefficient n, modulus of elasticity E, yield strength $R_{p0.2}$, tensile strength $R_m$, relative deformation in compressive e, relative deformation in strain ε, stress intensity factor K, energy of elastic deformation $W_e$, and energy of plastic deformation $W_p$.

The methodology of measurement according to the invention is universally useful for manual, table, and laboratory embodiments of instrument systems.

The indentation device can be used for quick inspection of the mechanical properties of materials directly on the site, e.g. gas pipelines, steel structures, etc., namely in the embodiment of the indentation device with its own loading mechanism or manual indentation device with a simple manual loading mechanism.

For measuring the mechanical properties of a material sample in aggressive environments such as in increased and decreased temperatures, aggressive or moist environments, or other, modifications of the indentation device are developed with prolonged indenter and a pan with sample holder inside.

The proposed indentation device is, due to its simplicity, also affordable for a wide range of applications in various branches of industry—from small workshops to large international industrial companies. It is also available in miniature sizes as a portable indentation "pen".

DESCRIPTION OF THE DRAWINGS

The invention is illustrated more closely by drawings which show.

EXAMPLES OF THE PREFERRED EMBODIMENTS OF THE INVENTION

It is understood that the hereinafter described and illustrated specific examples of the realization of the invention are presented for illustrative purposes and not as a limitation of the examples of the realization of the invention to the cases shown herein. Experts who are familiar with the state of technology shall find, or using routine experimentation will be able to determine, a greater or lesser number of equivalents to the specific realizations of the invention which are specifically described here.

Figure 1:
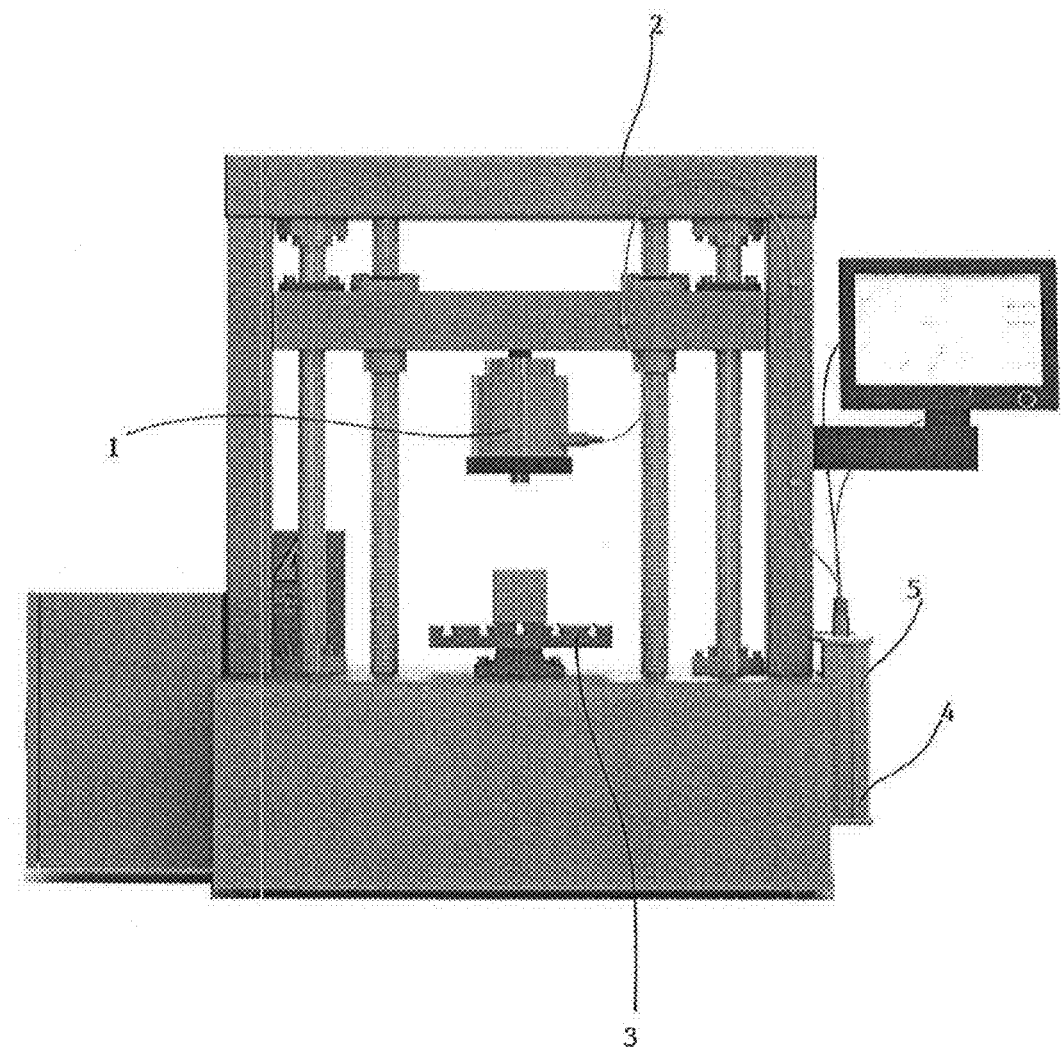
FIG. 1 view of the instrumented measurement system, with an indentation device clamped to the loading mechanism, computer and AD converter, FIG. 2 sectional view of the indentation device with loading mechanism in a combination of two load cells of different ranges, FIG. 3 sectional view of the indentation device with manual loading, FIG. 4 perspective view of the pushing segment with two supports, FIG. 5 perspective view of the holder of the first load cells for the indentation device according to FIG. 2, FIG. 6 perspective view of the rod with upper quadrangular part equipped with magnetic tape and an optical displacement sensor, FIG. 7 sectional view of the facing with extended supporting segment for measuring in aggressive environments, FIG. 8 view of the testing chamber for the tests in a simulated environment, FIG. 9 output of the instrumented measurement system after completing measurement, with indentation curve obtained by measuring using the indentation device according to FIG. 2, FIG. 10 output protocol of the instrumented measurement with an indentation curve, stress-strain diagram and the calculated of mechanical properties measured using the indentation device according to FIG. 2, FIG. 11 indentation curve obtained using indentation device according to FIG. 2, FIG. 12 stress-strain diagram measured using indentation device according to FIG. 2, FIG. 13 system for the calculations using the finite element method, FIG. 14 surface function F (P, E, Δ) with load P, modulus of elasticity E of the tested material, and Δ is the value of elastic deformation of the indenter, FIG. 15 graph showing the distribution of stress, FIG. 16 graph showing the distribution of plastic deformation, FIG. 17 CrAlN coating on a substrate of Cr—Ni steel, FIG. 18 damaged area with cracks at a given magnification.

The instrumented measuring system for measuring and determining the mechanical properties of materials by the indentation method is schematically illustrated in FIG. 1. The indentation device 1 is connected to a loading mechanism 2, for example to an existing hardness tester, to its own mechanism, etc. The loading mechanism 2 is provided with a table 3 for the sample. To the indentation device 1 there is connected, via an analog-to-digital converter 4, a computer 5 that also powers the indentation device 1 via a USB interface.

Figure 2:
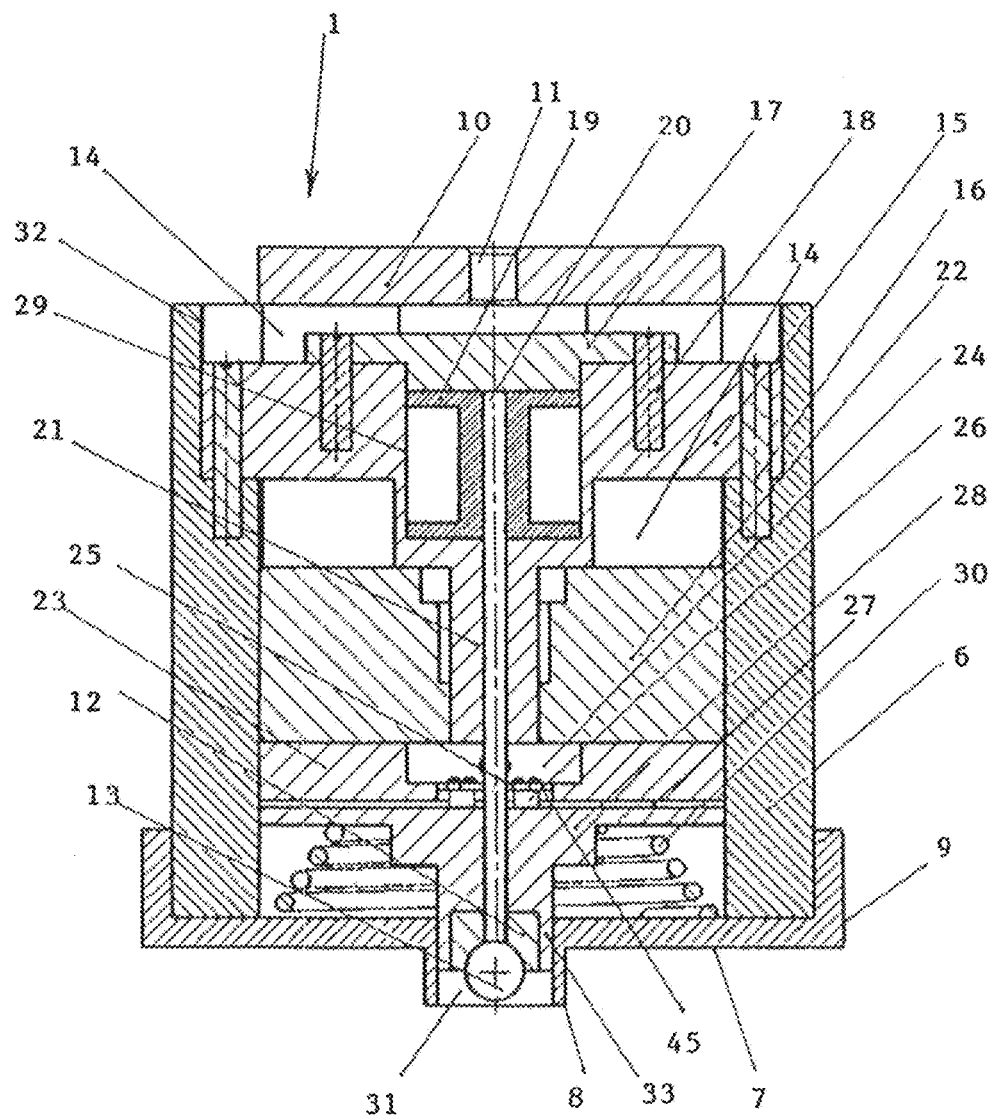

FIG. 2 shows an example of the realization of the indentation device 1 designed for measuring with maximum load up to 35 kN with high accuracy and measurement repeatability. The indentation device 1 comprises a housing 6 which, on the bottom side, is placed in a facing 7 with a peripheral flange 9 from which there protrudes a supporting segment 8 with a hole 31. In the hole 31 there is an exchangeable indenter 13 mounted in a holder 12. On the upper side of the housing 6 there is a pushing segment 10 equipped with a threaded hole 11 for clamping onto the hardness tester or another loading mechanism 2.

The load force acting on the pushing segment 10 is transmitted to the holder 12 of the indenter 13 through two supports 14 which abut on the second load cell 22 with a hole in the middle (e.g. "donut" type), displaceable arranged in the central part of the housing 6. The second load cell 22 is designed for larger loads up to 35 kN. The second load cell 22 pushes on the central pressure plate 23 which has a central recess 24 in which there are mounted the two first load cells 2 with deformable protrusions 26 extending from the underside of the center pressure plate 23. The height of the projections 26 define a known gap 27 between the central pressure plate 2 and the lower pressure plate 28 which has a guide collar 33 in which there is placed the holder 12 of the indenter 13 and which slides into a hole 31 of the supporting segment 8 upon loading the pushing segment 10 with the force load, wherein the indenter 13 protrudes from the supporting segment 8 and is pressed into the surface of the sample, upon which abuts the supporting segment 8. The reciprocal movement of the entire mechanism is provided by the first resilient member 30 comprising a compression spring between the lower pressure plate 28 and the facing 7.

For measuring a load force up to 150 N, the first load cells 25 are used, whose deformable protrusions 26 across the gap 27 abut on the central pressure plate 23. After achieving the maximum load force of 150 N, the first load cells 25, respectively their deformable protrusions 26 bend, whereby the deflection value is known and corresponds to the width of gap 27. After deformation and elimination of the gap 27, the central pressure plate 23 abuts directly onto the bottom pressure plate 2. The load force no longer acts through the first load cell 25, but through a second load cell 22 with a large measuring range. The first load cells 25 are mounted in a holder 45 which is mounted in the central recess 24 of the central pressure plate 3. There also may exist a variant of the device without the first load cells 25 when the accuracy of the second load cell 22 will be sufficient for calculating either a limited number of mechanical properties or the overall range with a small deviation.

The body of the holder 4 of the small load cells 25 is designed from a stability perspective so that even at maximum load its deflection does not influence the functionality of the first load cells 25.

The accuracy of the second load cell 22 must be at least 10 times less than the maximum load force of the first load cells 25. In the present example, the maximum load force of the first force sensors 25 is 150 N, the accuracy of the second load cell 22 must then be less than 15 N. This achieves the overlap of measured data for both types of load cells 72, 25 on the same range. For example, if the accuracy of the second load cell 22 is 4 N, then at a load of 200 N there will be, on the indentation curve, up to 150 N with 15000 points obtained from the first load cells 25 at intervals of 0.01 N, 150/4 points falling on the signal from the second load cell 22 and on the section from 150 to 200 N there will be (200−150)/4 additional points only from the second load cell 22.

The location of the tip of the indenter 13, or the indentation depth, is measured using a displacement sensor 19 onto which the movement of the indenter 13 is transmitted through the rod 2Q, which abuts against the indenter 13 and passes slidably through parts of the device to the displacement sensor 19 arranged in the upper part of the housing 6. The displacement sensor 19, the accuracy of which is at least 1 micron, has a hole arranged in the axis of the indenter 13, through which passes the rod 20 and by recording its displacement the penetration depth of the indenter fl is measured. The displacement sensor 19 may also be magnetic or different type with an accuracy of tens of microns.

To prevent the parts transmitting the displacement of the indenter from being affected by the load force, whereby their deformation would negatively affected the accuracy and reproducibility of measurement, the displacement sensor 19 is mounted in a special holder 15 which is fixed to the body of the housing 6. The housing 6 is cylindrical and in its upper part has an internal shoulder 32. Into this shoulder 32 there is mounted and fastened a holder 15 by means of bolts 16. In the holder 15 there is a central hole 29 in which there is arranged the displacement sensor 19 and which is closed from above by a cover 17 fastened by bolts 18 to the housing 15. The lower part of the holder 15 has a shoulder from which there extends a guide tube 21. This is mounted in the central hole of the second load cell 22 and has an inner cylindrical hole through which is guided the rod 2a into the displacement sensor 19.

When loading the indentation device 1 with force acting on the pushing segment 10, this force is transmitted through the supports 14 around the holder 15 of the displacement sensor 19 directly onto the second load cell 22. The location of the displacement sensor 19 in the holder 15 and the position of the holder 15 with respect to the housing 6 is completely fixed and unchanging. The rod 20 passes freely in the axis of the indenter 13 directly onto the displacement sensor 19, and is also not affected by any deformations that would evoke a load force. This is transmitted by the above described mechanism directly to the holder 12 of the indenter 13.

Between the holder 12 of the indenter 13 and the supporting segment 8 of the facing 7 there is arranged in the hole 31 a seal (not shown) which is resistant to aggressive environments and at the same time does not allow dirt or moisture to get into the indentation device 1. The sensors are thus protected against damage and elements that affect the measurement. The seal may be inserted into the bottom cover 14 or may be formed by a separate lower cover 14. The holes for the output for wiring and for bolting the indentation device 1 onto the loading mechanism 2 are also sealed. The housing 6, which is not burdened by the load force, is made of heat-resistant and corrosion-resistant material.

Since the indentation device 1 as per FIG. 2 enables accurate measurement over a wide range of loads up to 35 kN, it can be used to make measurements with all standard indenters 13, or with other impact bodies, such as e.g. indenters 13, Vickers, Knoop, Brinell with diameters of 1 mm, 2.5 mm, 5 mm, 10 mm, Berkovich, or indenters 13 for building materials.

Figure 3:
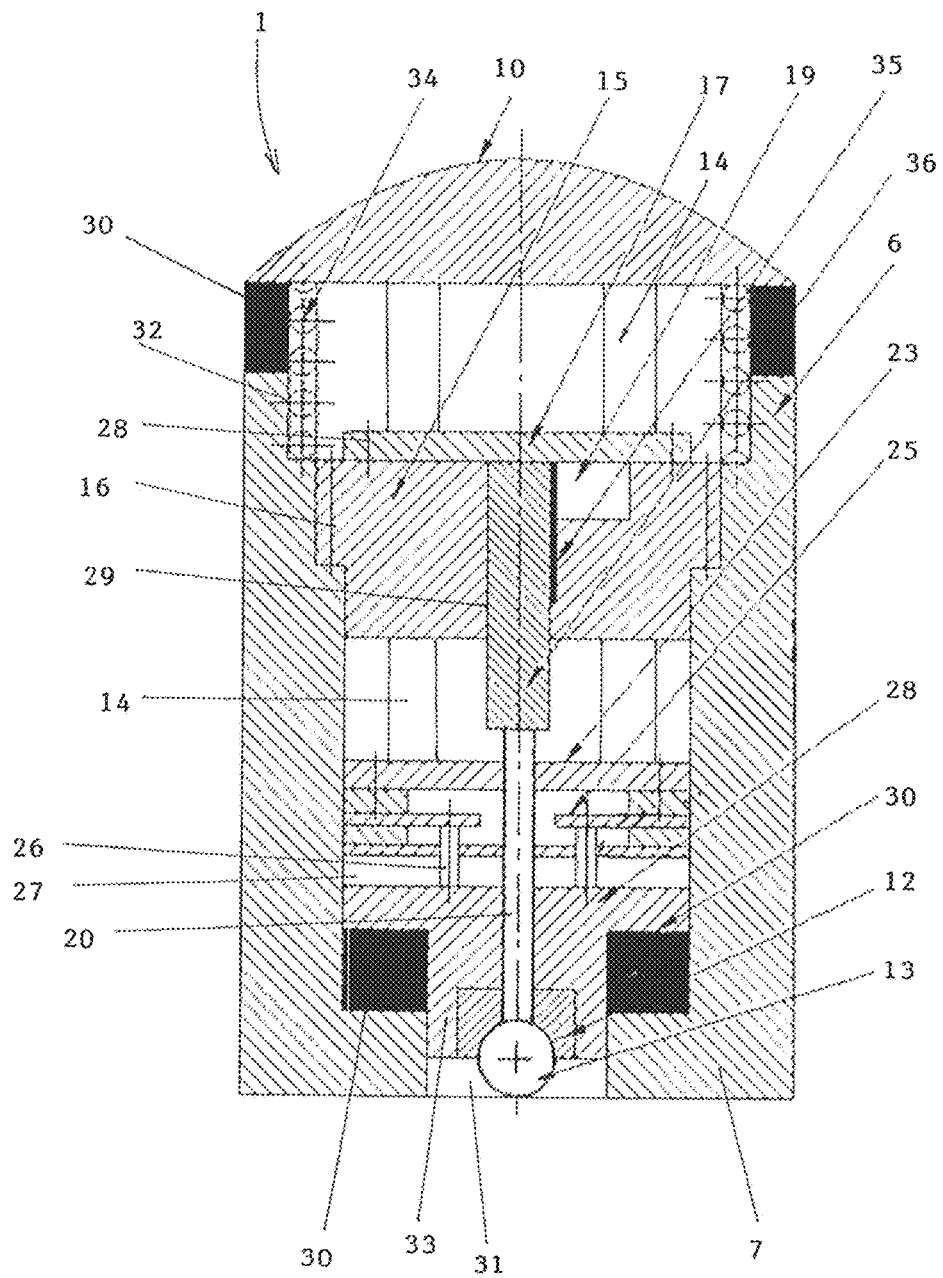

FIG. 3 shows an example of the realization of the indentation device 1 for measuring without a loading mechanism 2, wherein the load force is applied manually or by the linear displacement of a manipulator on a production line. Unlike the previous example, the manual indentation device 1 has a housing 6 with a facing 7 in one integrated unit, the facing 7 does not have a supporting segment 8, but is flat with a central hole 31 from which extends the indenter 13, set into the holder 12, which itself is seated in a guide collar 33 of the lower pressure plate 28 and moves together with it in the hole 31. Between the lower pressure plate 28 and the facing 7 there is the first resilient member 30 comprising a rubber pad. The pushing segment 10 in the upper part of the housing 6 has, in the manual embodiment, a convex ergonomic shape and abuts the housing 6 through the second resilient member 30, also comprising a rubber pad and also through the compression spring 34. Two supporters 14 extend around the holder 15 of the displacement sensor 19 and act directly on the central pressure plate 2 which bears the first two load cells 25 with deformable protrusions 26 which, via the gap 27, act on the lower pressure plate 28 and further on the holder 12 of the indenter 13. Measurement of the indentation depth is carried out principally as in the first example of the embodiment, using the rod 20 which is arranged in the axis of the indenter 13 and, without affecting the load force, transmits the motion of the indenter 13 to the displacement sensor 19 arranged in the holder 15 connected to the housing 6. The rod 20 has, in its upper part 6, a quadrangular cross-section and is guided in a quadrangular hole 29' in the holder 15. On the angular part of the rod 20 is a magnetic tape 35, opposite which there is arranged, in the holder 15, a magnetic displacement sensor 19. In another example of the embodiment, this may also be an optical or other sensor. The digitization of the measured signal is done using a small analog-to-digital converter and a smartphone or laptop with the appropriate software. For visual inspection of the actual value of the load force of manual loading, there is a small display on the housing 6.

The advantage of the manual indentation device 1 is its accuracy and the possibility to combine different measuring elements, thus allowing one to extend the device's range of use.

Figure 4:
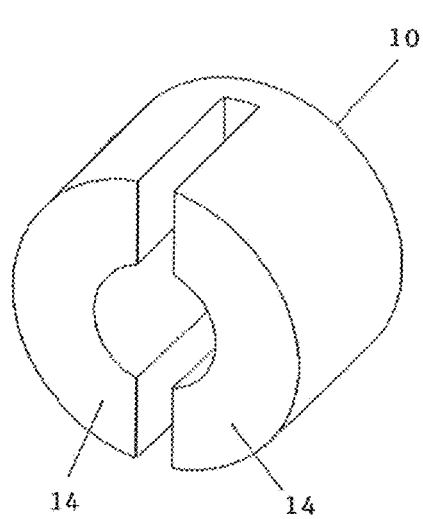

FIG. 4 shows an example of the realization of the pushing segment 10 to be bolted into the head of the hardness tester or other loading mechanism 2. The pushing segment 10 has two supports 14 which, at the indentation device 1 according to FIG. 2 push directly on the second load cell 22 of "donut" type. In the groove between the supports there is the holder 15 for the displacement sensor 19.

Figure 5:
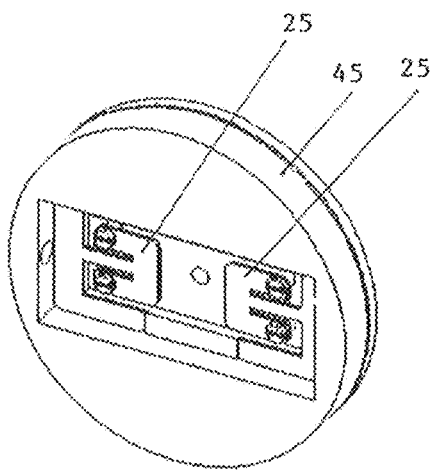

FIG. 5 shows a holder 45 of the first load cells 25 including the separate load cells 25 arranged in one plane for recording small loads up to 150 N with intervals of 0.01 N. The load cells 2 are attached to the holder 45 placed in the central pressure plate 23 and abut through the deformable protrusions 26 in the gap 27 on the underside of the pressure plate 28.

Figure 6:
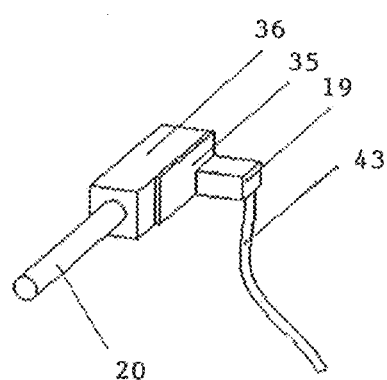

FIG. 6 shows an example of the realization of the optical displacement sensor 19 for the indentation device 1 shown in FIG. 3.

The rod 20 has an upper quadrangular part 36 on which there is a magnetic tape 35. From the optical displacement sensor 19 the read values are led through the conductor 43 through an analog-to-digital converter 4 to a computer 5 or a smartphone. In other examples of the embodiment, other known and suitable motion sensors may be used.

Figure 7:
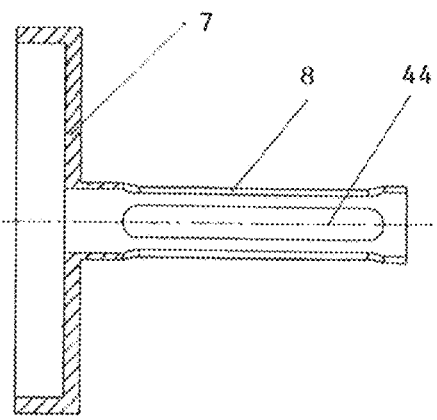

FIG. 7 shows an example of the realization of the facing 7 with an extended supporting segment 8 for the indentation device 1 according to FIG. 2. The length of the supporting segment 8 is several times longer than the dimension of the indenter 13. The supporting segment 8 is provided on the side with a recess 44. Similarly, the guide collar 33 of the lower pressure plate 28 is extended, not shown in FIG. 7. The extended supporting segment 8 is designed for measuring in aggressive environments, where e.g. increased temperature or chemicals may affect the actual indentation device 1.

Figure 8:
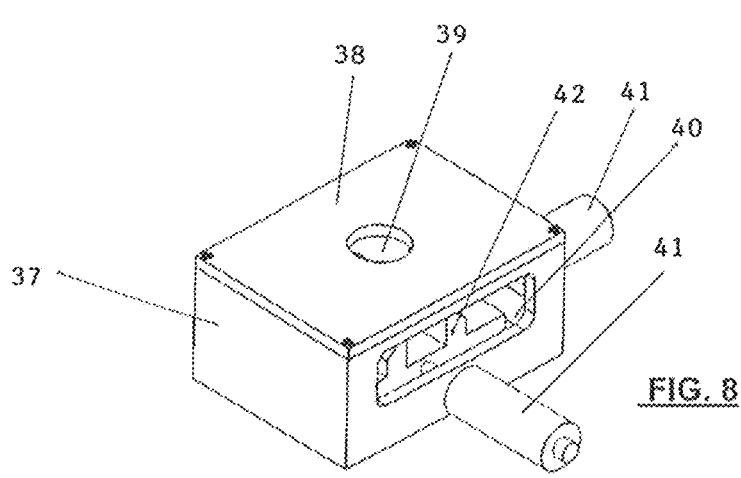

In some cases it is necessary, when measuring, to simulate operational conditions of the tested component. The accessory to the indentation device 1 designed for this is a chamber 37 for measuring samples in a simulated environment, shown in FIG. 8. The chamber 37 is provided with a cover 38 mounted on bolts 41, with a hole 39 for passage of the indenter 13 in the extended supporting segment 8 as per FIG. 7. Inside the chamber 37 there are jaws 42 for clamping the sample, slidable in two directions and controlled from the outside by micrometer bolts 41. In the wall of the chamber 37 is a window 40 of Plexiglas for observing the measuring.

Figure 9:
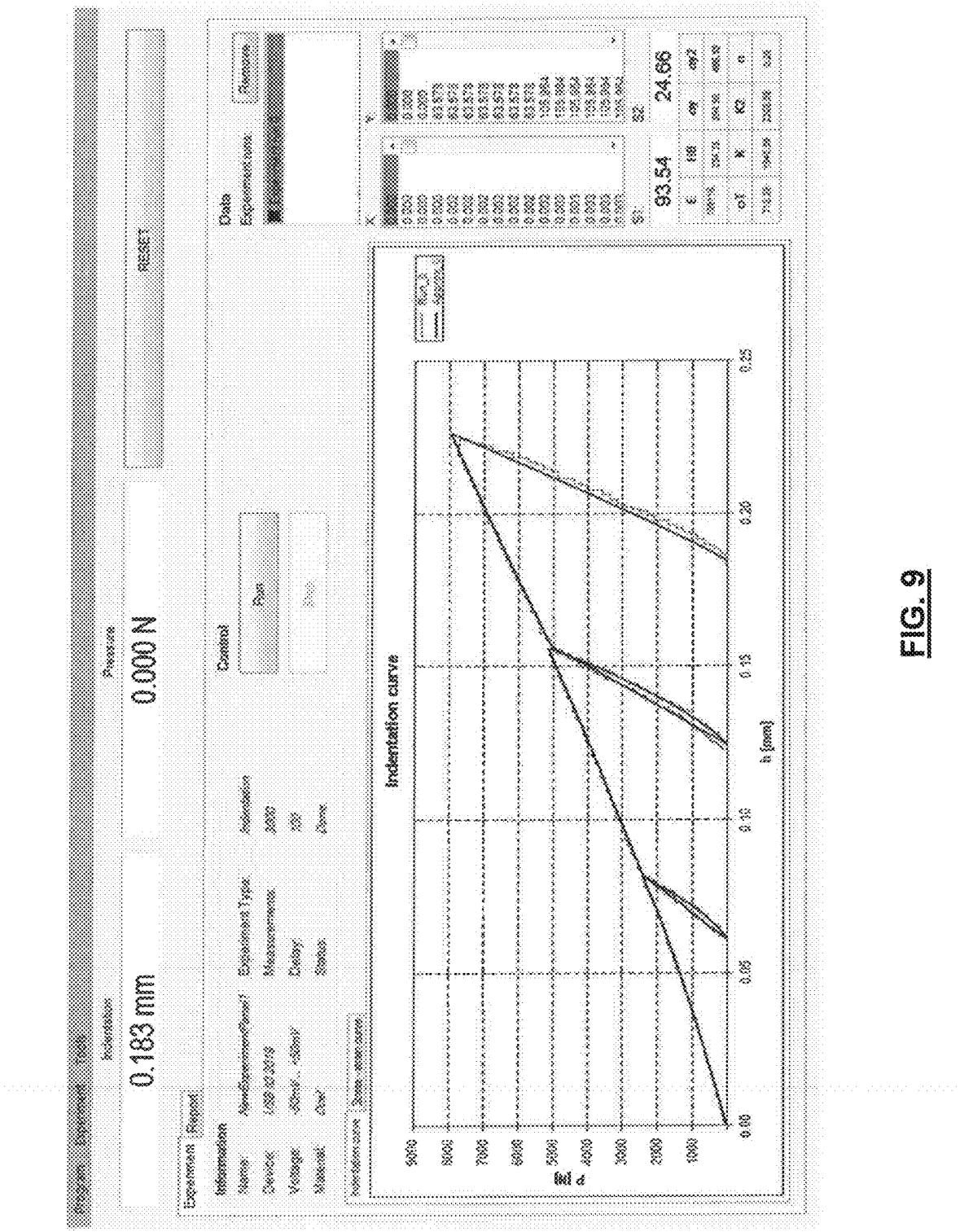

FIG. 9 shows an indentation curve obtained when measuring with the indentation device 1 according to FIG. 2. The software that processes the data from the analog-digital converter 4 shows a very accurate curve obtained from the values of the first load cells 25, then followed by display of values from the second load cell 22 of "donut" type. This construction obtains very accurate dependency at a low load, particularly in the elastic range, in which the modulus of elasticity E and yield strength $R_{p0.2}$ are calculated.

Figure 11:
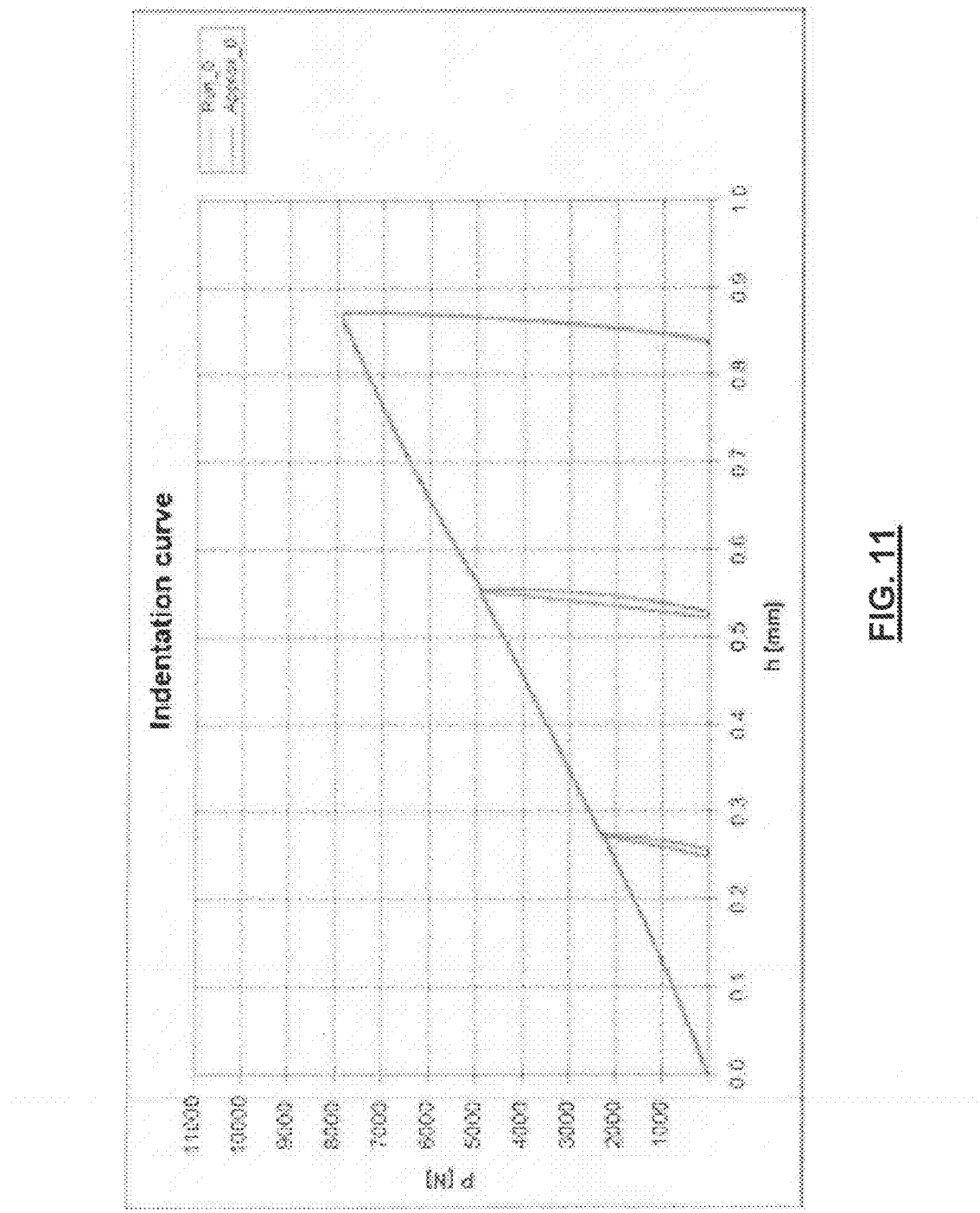

FIG. 11 displays a protocol with the indentation curve, the stress-strain diagram, and calculated mechanical properties. The protocol can be exported into *.pdf or *.xls file.

Figure 12:
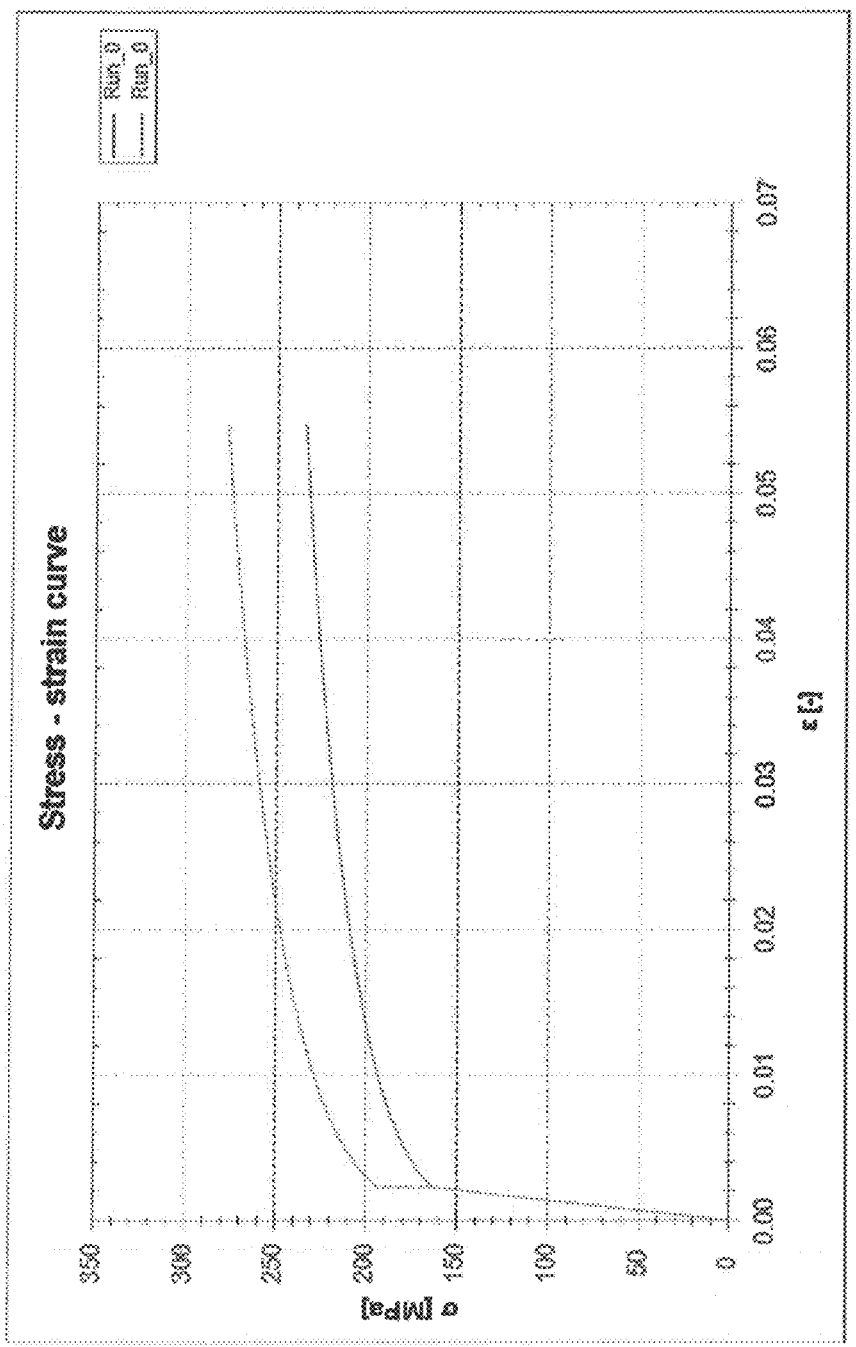
Figure 13:
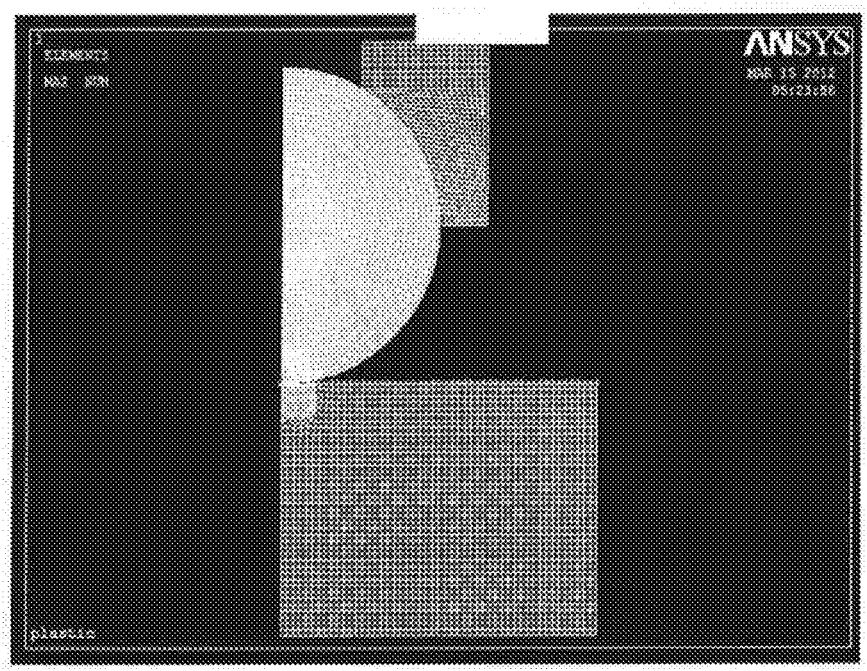
Figure 14:
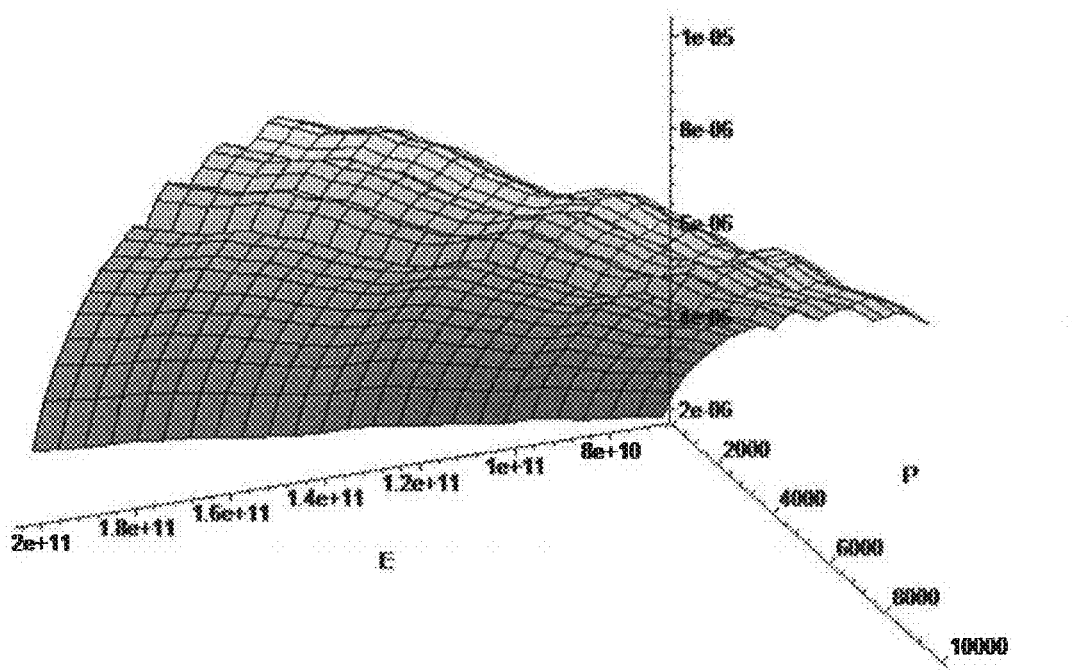
Figure 15:
Figure 16:
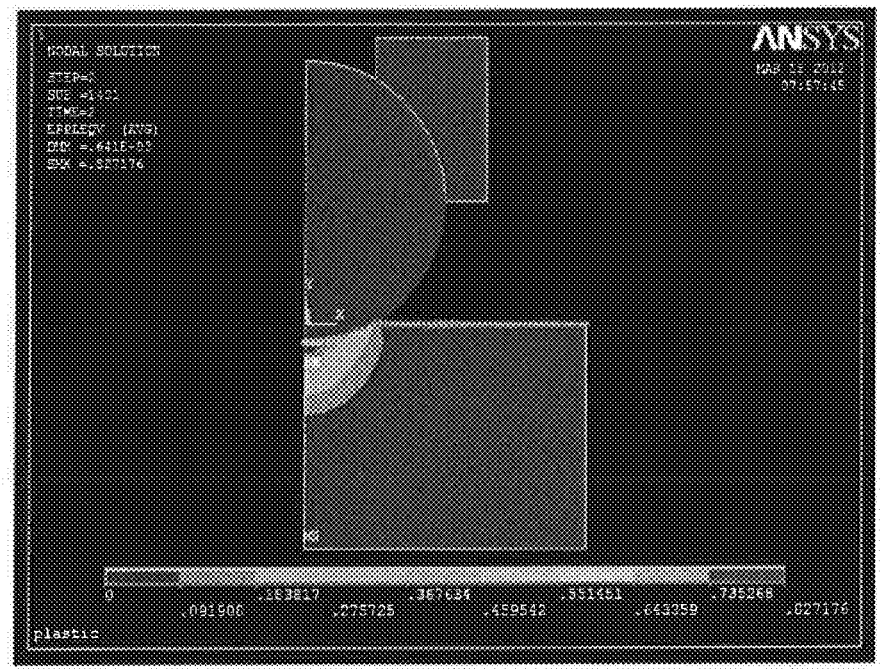
Figure 17:
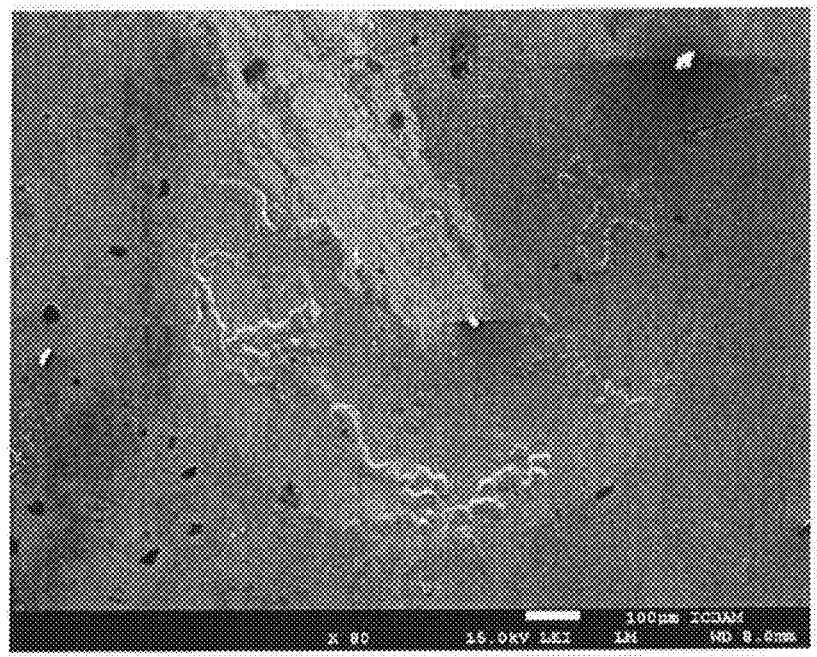

FIG. 12 shows the indentation curve. On the vertical axis the load is in N, on the horizontal axis the depth is in mm. For overall quality and accuracy of the measured indentation curve and the calculated parameters, the accuracy of the read data from both load cells 25, 22 of the displacement sensor 19 is important, so that the ratio of measurement points on the axis of the force and the depth, particularly at low loads, approaches the ideal. In the event that on a small section of the curve there will be 100 points gained from the data of the load cells 22, 25 and 3 points obtained from the data of the displacement sensor 19, the accuracy of the load cells 22, 25 will be influenced and in this case will be negligible.

For the actual determination of the mechanical properties of the material from the measured values of hardness, the computer 5 is equipped with measuring software. The application starts by verifying the ".exe" file. In the software interface, it is possible to select the type of indenter 13 and other parameters at the beginning of the measurement such as the type of converter 4, time of the experiment, test material, number of cycles, maximum load, speed of adjustment (displacement), etc. After starting the measurement, it is possible, in the graphics area, to monitor the ongoing rendering of the indentation curve from the beginning to the end of the measurement. After the termination of the measurement application, an approximation indentation curve is automatically created as shown in FIG. 11, the values of the mechanical and physical properties (E, HB, $Rp_{0.2}$, $R_m$, K, n, $W_e$, $W_p$) are calculated, and the stress-strain diagram is plotted. The process can be monitored and observed by opening the tab "Stress-strain curve". The tab "Report" allows one to save the measured values and curves in a ".pdf" or ".xls" file.

For the actual determination of mechanical properties, the algorithms and techniques described below are used. In these processes, the following signs, symbols, and abbreviations are used:

HB—Brinell hardness
HM—Martens hardness
HV—Vickers hardness
$P_{1\ldots m}$—maximum load value in the cycle
$h_{1\ldots m}$—indentation depth after unloading
D—Brinell indenter diameter (1; 2.5; 5; 10)
a—contact radius of indentation
n—material hardening coefficient
E—tensile elasticity modulus
$R_{p0.2}$—yield strength
$R_m$—tensile strength
e—relative deformation in compression
ε—relative deformation in strain
C=2.8 . . . 3.2 compression coefficient
K—stress intensity factor
$W_e$—energy of elastic deformation
$W_p$—energy of plastic deformation
$h_s$—depth of the plastic zone under the indenter
$\sigma_r$—yield strength,
d—indentation diameter
$\sigma_i$—stress intensity
$\varepsilon_i$—intensity of deformation
$u_p$—specific energy
$K_I$—stress intensity factor
$K_{IC}$—fracture toughness The determination of the mechanical properties of materials by the indentation method according to the invention is performed as follows. First, a calculation of the hardness value is carried out according to the Brinell method in each cycle:

$$HB_{1\ldots m} = \frac{P_{1\ldots m}}{\pi \cdot D \cdot h_{1\ldots m}} \quad (1)$$

where $P_{1\ldots m}$ is the maximum load value in the cycle, $h_{1\ldots m}$ is the depth of indentation after unloading, D—the diameter of the indenter 13 (1; 2.5; 5; 10). Then, using these values, the coefficient of hardness of material n is calculated, according to the following formula (2)

$$n = \frac{HB_2 - HB_1}{(HB_m - HB_{m-1}) \cdot (m-1)} \quad (2)$$

The calculation of the modulus of elasticity E and the yield strength Re is carried out in the area of elastic deformation from 0 to $P_1$. The contact radius a according to the formulas (3)

$$a = \sqrt{2 \cdot R \cdot h - h^2} = \sqrt{D \cdot h - h^2} \quad (3)$$

and deformation e and ε according to (4)

$$e = 0,2\frac{a}{D}; \varepsilon = \frac{h}{D} \quad (4)$$

Martens hardness is calculated by using formula (5)

$$HM = \frac{P}{\pi \cdot a^2} \quad (5)$$

Then, by analogy on the basis of Hook's law, one can calculate the modulus of elasticity E [MPa]

$$E = \frac{HM}{e} \quad (6)$$

Figure 18:
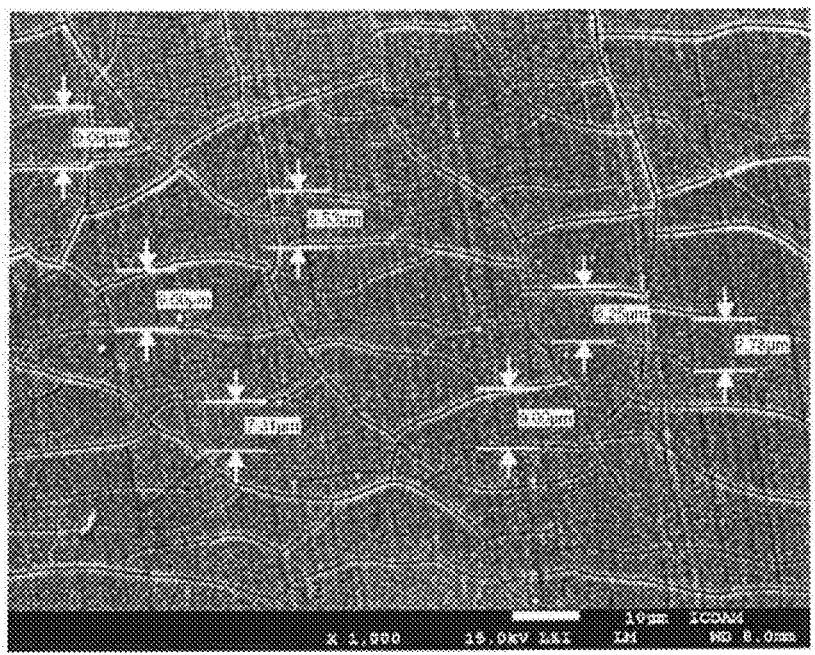

It is to be expected that the ascertained values will have some deviation because the exact value must be chosen with regard to the type of material being tested (e.g. for steel 210 GPa, aluminum 70 Gpa, etc.). Using the same method, the modulus of elasticity E of thin films is calculated on part of the indentation curve to the break of the coating (e.g. PAPVD/CVD, etc.) into the substrate. Breaking the coating can be detected by a significant decrease in the modulus of elasticity E which is seen on the relationship F(a)=E in FIG. 18 and FIG. 19.

For the calculation of the yield strength, the value HM must be obtained, at which $\varepsilon_{0.2} \approx 0.002$. This value is indicated as $HM_{0.2}$, then $$R_{p0.2} = C \cdot HM_{Y0.2} \quad (7)$$

in certain cases can be substituted by $$R_{p0.2} = E \cdot \varepsilon_{0.2} \quad (8)$$

C=2.8 ... 3.2 compression coefficient

The value of tensile strength $R_m$ is calculated according to the formula (9)

$$R_m = C \cdot HB_1 \quad (9)$$

The value of the stress intensity factor K can be calculated according to formula (10)

$$K = R_{0.2} \left( \frac{\varepsilon_{0.2}}{R_{0.2}} \right)^n \quad (10)$$

Figure 10:
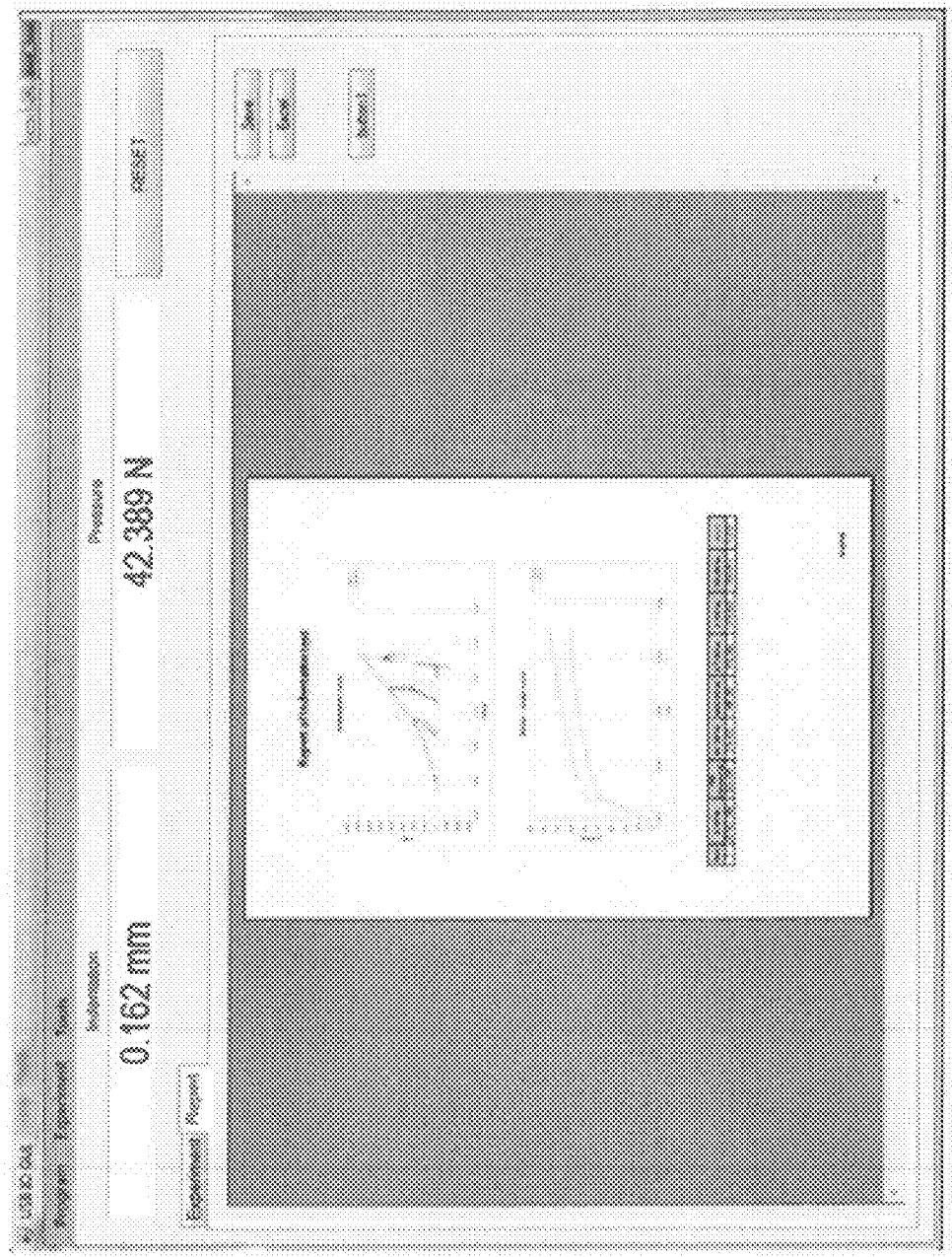

The curve "stress-strain" according to FIG. 10 can be obtained from the calculation according to the system of equations (11)

$$\begin{cases} R = E \cdot \varepsilon, & R < R_{p0.2}, \quad (I) \\ R = K \cdot \varepsilon^n, & R \geq R_{p0.2}, \quad (II) \end{cases} \quad (11)$$

The energy of elastic $W_e$ and plastic $W_p$ deformation is calculated using the conventional method as the area under the curve of indentation. In cyclic measurement, this will be the first section before the load $P_1$.

When determining the mechanical properties of building materials, the procedure is the same, but it is preferred to use an ultrasonic probe to control the porosity of the internal volume of the material.

To determine the elastic deformation of the indenter 13 in the holder 12, calculations are performed using the finite element within the ANSYS program. From these calculations there were obtained values of elastic deformation Δ of the indenter 13 at different values of the modulus of elasticity of sample E with the applied load P. These values are entered into a mathematical software, such as Maple, where their approximation is made using cubic "spline functions" depending on the elastic deformation. Also processed is the surface F (P, E, Δ). From this function, the value of elastic deformation of the indenter 13 can be determined for different combinations of values of the modulus of elasticity of the sample and load.

Determining the fracture toughness can be based on the method of estimating the fracture toughness of steel based on contact deformation. First, calculate the depth of the plastic zone under the indenter according to the relationship:

$$h_s = \sqrt{\frac{P}{2\sigma_T} - 1, 2\left(\frac{d}{2}\right)^2} \quad (12)$$

where P—load value, $\sigma_T$—yield strength, d—diameter of the indentation

Then, the intensity of stress $\sigma_i$ and deformation $\varepsilon_i$ are calculated according to the known formulas of contact mechanics, or a calculation using finite element modeling.

Next, the plastic deformation energy is calculated according to equation:

$$u_i = \frac{\sigma_T + \sigma_i}{2} \times \varepsilon_i \quad (13)$$

The integration of $u_i$ from 0 to $h_s$ yields $u_p$:

$$u_p = \int_0^{h_s} u_i \, dx \quad (14)$$

where $u_p$ is the total energy.

The value of the fracture toughness $K_{IC}$ and $\sqrt{u_p}$ are linearly dependent.

When determining the fracture toughness of the coating, the procedure is as follows. The density of cracks that occur after indentation of the indenter can be described as density of violation. Based on a metallographic analysis, this value is determined by the grid method. The energy of the damage is equal to the density of the damage (density of the fracture surfaces) times the energy of the fracture surface. $K_I^2$ is equal to the energy of the fracture surface G, times the elastic modulus E.

$$K_I^2 = G \cdot E \quad (15)$$

INDUSTRIAL APPLICABILITY

An indentation device, instrumented measurement system, and measuring method according to the invention can be used wherever there is a need to measure or inspect the mechanical properties of materials by the indentation method. The indentation device can be used with integrated loading mechanism, or it can be mounted to a tensile machine, or hardness tester, or other loading mechanism, thus giving it new use. On the production line, the indentation device shall find application in rapid quality control of products or semi-finished products. The advantage of this device is also its use in the evaluation of residual life based on changes in mechanical properties of different components such as pipelines, pressure vessels etc. The indentation device can be used as a separate and compact mobile measuring device or in combination with a manipulator, a linear motor, or a robot.

OVERVIEW OF THE POSITIONS USED IN THE DRAWINGS

1 indentation device
2 loading mechanism
3 sample table
4 analog-digital converter
5 computer
6 housing
7 facing
8 supporting segment of the facing
9 peripheral flange
10 pushing segment
11 threaded hole
12 indenter holder
13 indenter
14 support
15 displacement sensor holder
16 displacement sensor holder bolt
17 displacement sensor holder cap
18 cap bolt
19 displacement sensor
20 rod 21 guide tube
22 second load cell
23 central pressure plate
24 recess of central pressure plate
25 first load cell
26 deformable protrusion of the first load cell
27 gap
28 bottom pressure plate
29, 29' hole in the displacement sensor holder
30, 30' resilient member
31 hole in the facing
32 internal shoulder
33 guide collar
34 compression spring
35 magnetic tape
36 upper quadrangular part of the rod
37 chamber for measuring samples in a simulated environment
38 chamber cap
39 hole for indenter
40 window
41 bolt
42 sliding jaw
43 conductor
44 recess
45 holder for the first load cells

The invention claimed is:

1. An indentation device for measuring the mechanical properties of materials, comprising a housing provided with a facing with a hole, a holder for an indenter mounted that is capable of sliding in the hole of the facing, a rod abutting the indenter via a displacement sensor, a load cell, and a movable pushing segment for loading the holder with the indenter, wherein a holder for the displacement sensor is rigidly connected to the housing in which there is slidably positioned a rod passing to the displacement sensor arranged in the holder in the axis of the indenter without deformation of all components through which a loading mechanism is dropped on the indenter; the movable pushing segment in the upper part of the housing is provided with at least one support extending around the holder and engaging with a central pressure plate arranged slidably in the housing and supporting at least one first load cell with deformable protrusions which cross a gap and abut a bottom pressure plate arranged slidably in the housing and connected with the holder of the indenter, wherein between the bottom pressure plate and the facing there is arranged a first resilient member, and the central pressure plate and the bottom pressure plate are provided with holes for passage of the rod into the holder.

2. The indentation device according to claim 1, wherein the housing is of cylindrical shape with an internal shoulder formed above, in which by means of bolts there is mounted the holder in whose center there is created a hole for the rod, in which there is arranged the displacement sensor, wherein the hole is, on the upper side of the holder, covered by a cap mounted by bolts to the holder.

3. An indentation device for measuring the mechanical properties of materials, comprising a housing provided with a facing with a hole, a holder for an indenter mounted that is capable of sliding in the hole of the facing, a rod abutting the indenter via a displacement sensor, a load cell, and a movable pushing segment for loading the holder with the indenter, wherein inside the housing there is arranged a holder for the displacement sensor, rigidly connected to the housing in which there is slidably positioned a rod passing to the displacement sensor arranged in the holder in the axis of the indenter; the movable pushing segment in the upper part of the housing is provided with at least one support extending around the holder and engaging with a central pressure plate arranged slidably in the housing and supporting at least one first load cell with deformable protrusions which cross a gap and abut a bottom pressure plate arranged slidably in the housing and connected with the holder of the indenter, wherein between the bottom pressure plate and the facing there is arranged a first resilient member, and the central pressure plate and the bottom pressure plate are provided with holes for passage of the rod into the holder, wherein two supports abut the central pressure plate via at least one second load cell, arranged on a middle pressure plate, wherein the accuracy of the second load cell is at least 10 times lower than the maximum load force of the first load cell, and the value of the maximum deformation of the deformable protrusions of the first load cell at maximum load corresponds to the known width of the gap.

4. The indentation device according to claim 3, wherein the measuring range of the first load cell is up to 150 N and the measuring range of the second load cell is up to 35 kN.

5. The indentation device according to claim 4, wherein the holder of the sensor has, at its bottom part, a central guide tube, placed in the central hole of the second load cell and the central pressure plate is provided with a central recess in which there are arranged the two first load cells around the rod, which passes through the recess and is slidably positioned in the guide tube.

6. An indentation device for measuring the mechanical properties of materials, comprising a housing provided with a facing with a hole, a holder for an indenter mounted that is capable of sliding in the hole of the facing, a rod abutting the indenter via a displacement sensor, a load cell, and a movable pushing segment for loading the holder with the indenter, wherein inside the housing there is arranged a holder for the displacement sensor, rigidly connected to the housing in which there is slidably positioned a rod passing to the displacement sensor arranged in the holder in the axis of the indenter; the movable pushing segment in the upper part of the housing is provided with at least one support extending around the holder and engaging with a central pressure plate arranged slidably in the housing and supporting at least one first load cell with deformable protrusions which cross a gap and abut a bottom pressure plate arranged slidably in the housing and connected with the holder of the indenter, wherein between the bottom pressure plate and the facing there is arranged a first resilient member, and the central pressure plate and the bottom pressure plate are provided with holes for passage of the rod into the holder, wherein the housing is of cylindrical shape with an internal shoulder formed above, in which by means of bolts there is mounted the holder in whose center there is created a hole for the rod, in which there is arranged the displacement sensor, wherein the hole is, on the upper side of the holder, covered by a cap mounted by bolts to the holder, and wherein the facing has a peripheral flange in which is set the housing and a central supporting segment with the hole, in which there is slidably positioned a guide collar of the bottom pressure plate in which there is mounted the holder of the indenter, and the first resilient member is formed by a pressure spring arranged between the lower pressure plate and the facing.

7. The indentation device according to claim 1, wherein the rod passes through the central hole of the displacement sensor, which is touch sensitive, magnetic, or other type.

8. An indentation device for measuring the mechanical properties of materials, comprising a housing provided with a facing with a hole, a holder for an indenter mounted that is capable of sliding in the hole of the facing, a rod abutting the indenter via a displacement sensor, a load cell, and a movable pushing segment for loading the holder with the indenter, wherein inside the housing there is arranged a holder for the displacement sensor, rigidly connected to the housing in which there is slidably positioned a rod passing to the displacement sensor arranged in the holder in the axis of the indenter; the movable pushing segment in the upper part of the housing is provided with at least one support extending around the holder and engaging with a central pressure plate arranged slidably in the housing and supporting at least one first load cell with deformable protrusions which cross a gap and abut a bottom pressure plate arranged slidably in the housing and connected with the holder of the indenter, wherein between the bottom pressure plate and the facing there is arranged a first resilient member, and the central pressure plate and the bottom pressure plate are provided with holes for passage of the rod into the holder, wherein the pushing segment is provided with a threaded hole for connection to the loading mechanism.

9. The indentation device according to claim 6, wherein the length of the supporting segment is greater than the length of the holder of the indenter, and the supporting segment is provided with a lateral recess.

10. An indentation device for measuring the mechanical properties of materials, comprising a housing provided with a facing with a hole, a holder for an indenter mounted that is capable of sliding in the hole of the facing, a rod abutting the indenter via a displacement sensor, a load cell, and a movable pushing segment for loading the holder with the indenter, wherein inside the housing there is arranged a holder for the displacement sensor, rigidly connected to the housing in which there is slidably positioned a rod passing to the displacement sensor arranged in the holder in the axis of the indenter; the movable pushing segment in the upper part of the housing is provided with at least one support extending around the holder and engaging with a central pressure plate arranged slidably in the housing and supporting at least one first load cell with deformable protrusions which cross a gap and abut a bottom pressure plate arranged slidably in the housing and connected with the holder of the indenter, wherein between the bottom pressure plate and the facing there is arranged a first resilient member, and the central pressure plate and the bottom pressure plate are provided with holes for passage of the rod into the holder, wherein it includes an external chamber for measuring samples of material in a simulated environment, the chamber is closed by a removable cover with a hole for the indenter, inside the chamber there are slidable jaws for holding a sample and which are connected with the micrometric bolts projecting from the housing of the chamber, and the chamber is further provided with a window for monitoring the sample.

11. An indentation device for measuring the mechanical properties of materials, comprising a housing provided with a facing with a hole, a holder for an indenter mounted that is capable of sliding in the hole of the facing, a rod abutting the indenter via a displacement sensor, a load cell, and a movable pushing segment for loading the holder with the indenter, wherein inside the housing there is arranged a holder for the displacement sensor, rigidly connected to the housing in which there is slidably positioned a rod passing to the displacement sensor arranged in the holder in the axis of the indenter; the movable pushing segment in the upper part of the housing is provided with at least one support extending around the holder and engaging with a central pressure plate arranged slidably in the housing and supporting at least one first load cell with deformable protrusions which cross a gap and abut a bottom pressure plate arranged slidably in the housing and connected with the holder of the indenter, wherein between the bottom pressure plate and the facing there is arranged a first resilient member, and the central pressure plate and the bottom pressure plate are provided with holes for passage of the rod into the holder, wherein the pressure segment is adapted for handling without a loading mechanism, the first resilient member is formed by a rubber pad, and between the pressure segment and the housing there is provided a second resilient member also comprising a rubber pad and a return spring.

12. The indentation device according to claim 11, wherein the rod is quadrangular in its upper part, is provided with a magnetic tape and is slidably positioned in a quadrangular hole in the holder of the displacement sensor, wherein opposite the magnetic tape in the holder there is arranged the displacement sensor comprising a magnetic sensor.

13. The indentation device according to claim 11, wherein the housing forms an integral unit with the facing, the lower base of the facing is straight, the upper surface of the pressure segment is convex, and the lower pressure plate has a guide collar in which there is mounted the holder of the indenter which is slidably positioned in the hole of the facing.

14. The instrumented measurement system for measuring the mechanical properties of materials that includes the indentation device, the loading mechanism and components for analyzing the indention data, a table for the sample, an analogue-digital converter, and a computer, wherein the indentation device is formed according to claim 1.

* * * * *